United States Patent [19]

Armstrong

[11] 4,038,754
[45] Aug. 2, 1977

[54] ORTHODONTIC APPLIANCE GUARD

[75] Inventor: Maclay M. Armstrong, Seattle, Wash.

[73] Assignee: Northwest Orthodontics, Inc., Seattle, Wash.

[21] Appl. No.: 661,973

[22] Filed: Feb. 27, 1976

[51] Int. Cl.² .............................................. A61C 7/00
[52] U.S. Cl. ................................................. 32/14 D
[58] Field of Search .................... 32/14 A, 14 B, 14 C, 32/14 D

[56] References Cited

U.S. PATENT DOCUMENTS 1,039,683  10/1912  Angle ................................... 32/14 A

FOREIGN PATENT DOCUMENTS 697,818   9/1940  Germany ............................. 32/14 A
667,040   6/1938  Germany ............................. 32/14 A
2,239,807 3/1973  Germany ............................. 32/14 A Primary Examiner—Robert Peshock
Attorney, Agent, or Firm—Robert W. Beach

[57] ABSTRACT

Danger of serious injury caused by sharp projections on a displaceable intraoral orthodontic appliance is avoided, or at least greatly decreased, by providing guards alongside such projections or by substituting guards for such projections. Such a guard can be a wire having an enlarged blunt end portion preferably in the form of a loop. The guard wire is mounted alongside the sharp projection of the orthodontic appliance, such as an inner bow anchor tip, and projects beyond such tip. In some instances, the sharp tip, such as a spur, can simply be replaced by a wire having a blunt tip.

23 Claims, 43 Drawing Figures

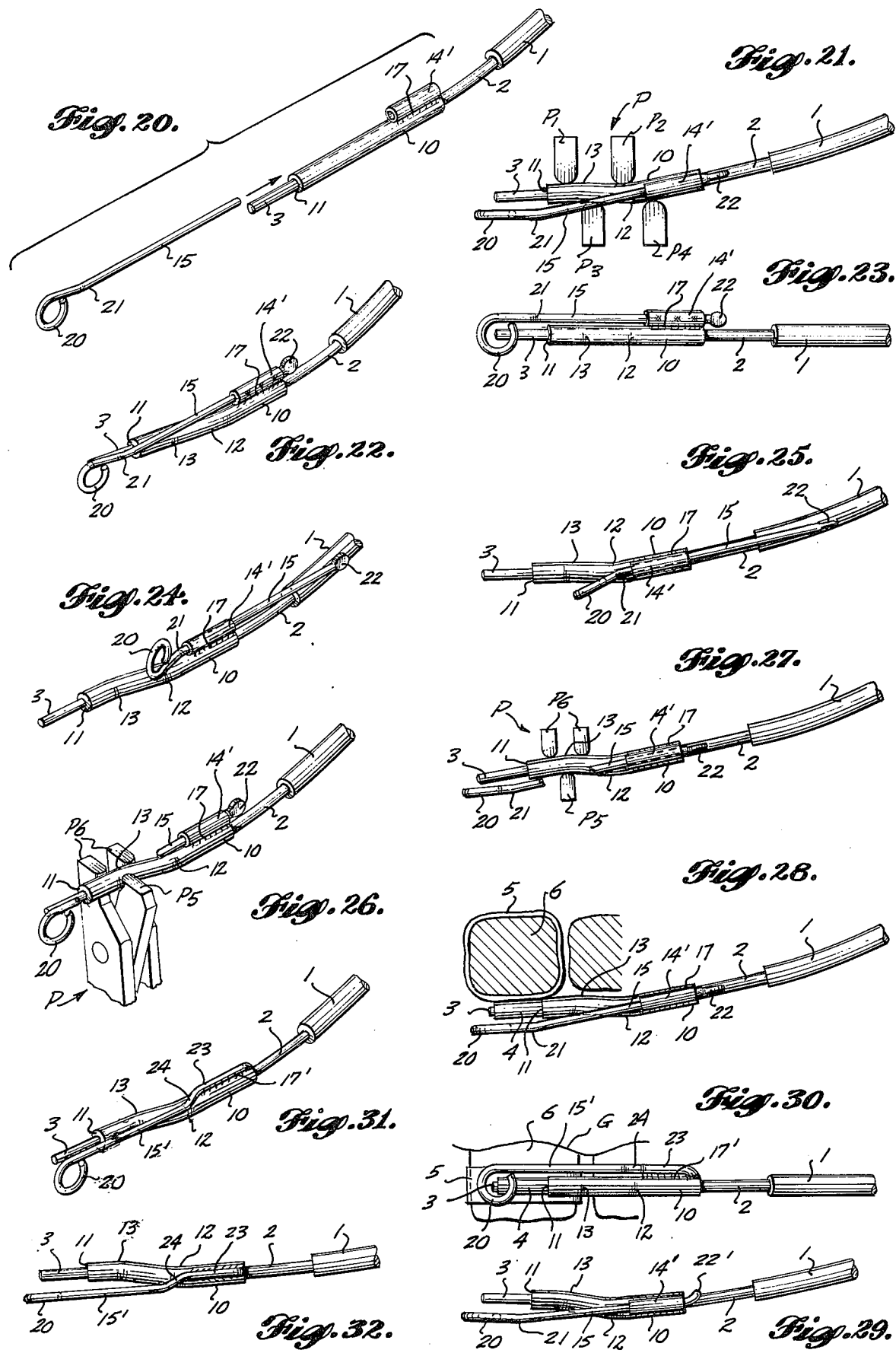

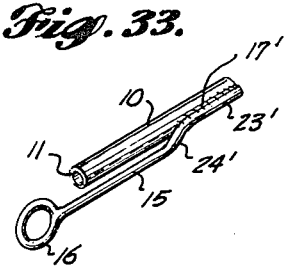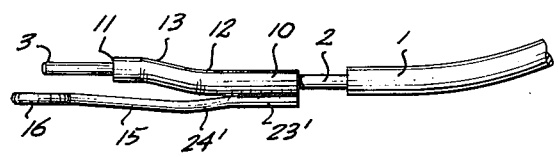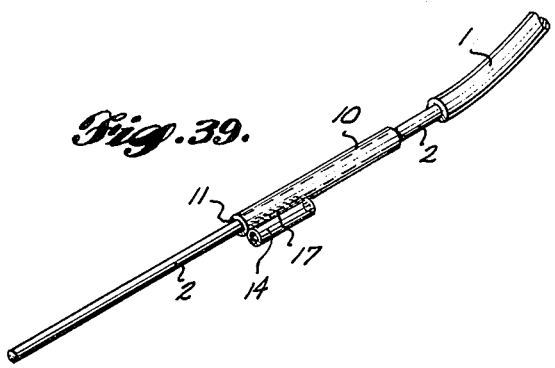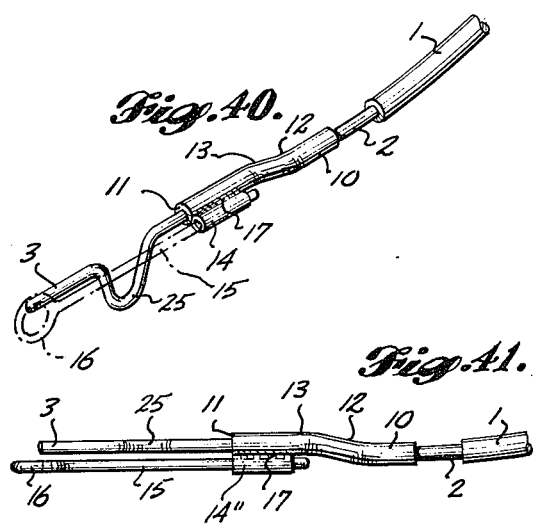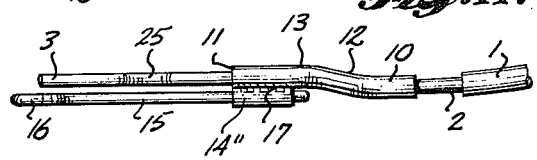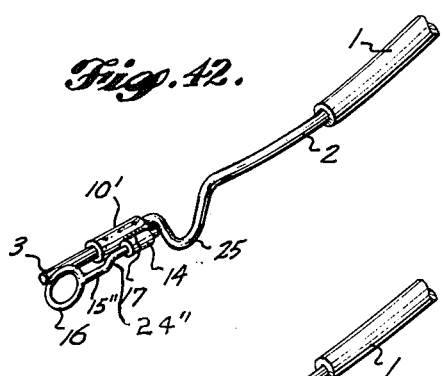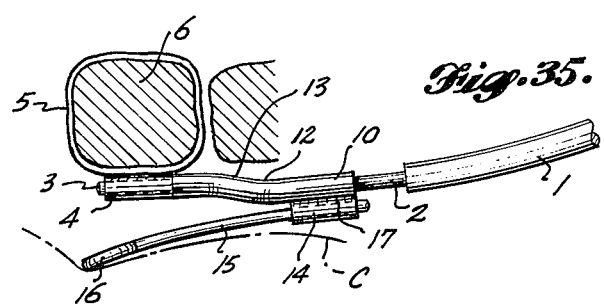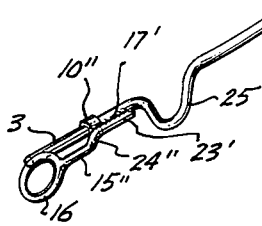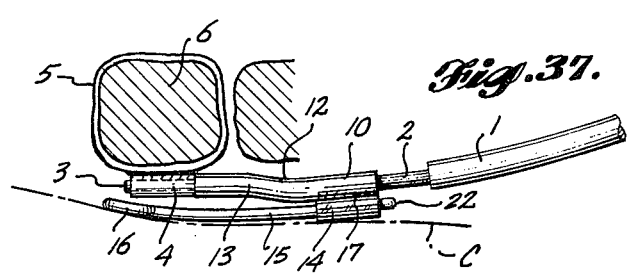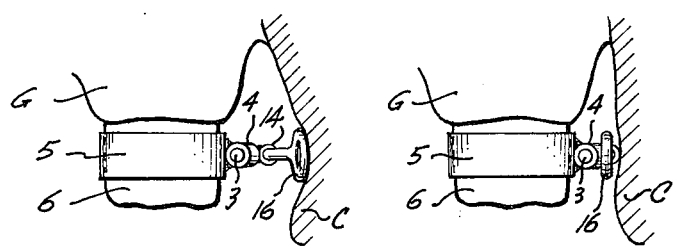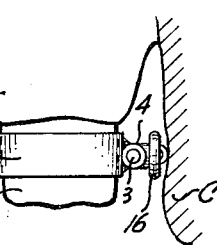

4,038,754

ORTHODONTIC APPLIANCE GUARD

BACKGROUND OF THE INVENTION

1. Field of the Invention

The present invention relates to orthodontic appliances, and particularly to intraoral components of orthodontic headgear such as the inner bow of a double facebow utilized to exert a rearward force on orthodontic elements secured to the teeth.

2. Prior Art

The principal objective of orthodontic treatment is to alter the relationship of teeth so as to provide proper relative disposition and articulation of the teeth in the upper and lower jaws. In order to accomplish this objective, it is desirable in many instances to apply an external force to an intraoral component of headgear, which component is attached to teeth, usually those of the upper jaw, and more particularly to upper molars.

A conventional intraoral component for applying force to teeth in orthodontic treatment is a double facebow, including an inner bow having tips engageable in sockets of bands encircling molars and an outer bow extending outward of the mouth to which tension force can be applied. Such facebow is usually removable by the patient simply by disconnecting the force-supplying mechanism from the outer bow and pulling the inner bow out of the mouth without the necessity of disconnecting any securing element. Conventionally, the facebow applies rearward pressure to the molar bands by the tips of the inner bow exerting thrust on the sockets in which they are received. Such tips are straight, rather sharp wires.

Instances have occurred where the facebow has been pulled to withdraw the inner bow from the mouth without first disconnecting the force-applying mechanism, and the facebow has then been released resulting in the force-supplying means driving the facebow toward the face so that the tips of the inner bow are impelled toward the face with sufficient force to penetrate the flesh, or even the eyes, and cause injury. In addition to the inner bow of the face bow having ends in the form of sharp tips, such a facebow may have a sharp spur projecting inward from its central portion for engaging and lifting the central portion of the upper arch wire for intruding the front teeth.

SUMMARY OF THE INVENTION

It is the principal object of the present invention to provide guard means for projections on intraoral orthodontic devices whether such a projection itself is formed as a guard, or a guard separate from the projection is provided alongside such projection.

Another object is to provide such guard means which will be compact and unobtrusive, yet will be effective.

It is also an object to provide such guard means which will not detract from or interfere with the usefulness of the orthodontic appliance.

A further object is to provide guard means which can readily be applied to a conventional intraoral orthodontic appliance without interfering appreciably with the fitting, placement or removal of such appliance.

The foregoing objects can be accomplished by forming a projection on an intraoral orthodontic component with an enlarged blunt end portion, or by providing alongside a projection or an orthodontic intraoral component a guard wire having an enlarged blunt end portion which projects beyond the end of the sharp projection. The blunt end portion may be in the form of a loop.

BRIEF DESCRIPTION OF THE DRAWINGS

FIG. 20 is a top perspective of an end portion of an inner bow component of a double facebow showing a modified type of guard construction with parts in exploded relationship.

FIG. 21 is a plan, FIG. 22 is a top perspective and FIG. 23 is a side elevation of the structure shown in FIG. 20 but with parts in assembled relationship. FIG. 24 is top perspective and FIG. 25 is a plan of the same structure showing parts in a different relationship. FIG. 26 is a top perspective and FIG. 27 is a plan with parts broken away of the same structure illustrating a forming procedure of the inner bow end portion. FIG. 28 is a plan of the same structure shown in operative placement with respect to teeth.

FIG. 29 is a plan of an end portion of an inner bow component of a double facebow showing a slightly modified type of guard structure.

FIG. 30 is a side elevation, FIG. 31 is a top perspective and FIG. 32 is a plan of an end portion of an inner bow component of a double facebow showing a further modified type of guard structure.

FIG. 33 is a top perspective and FIG. 34 is a plan of an end portion of an inner bow component of a double facebow showing another type of guard structure.

FIG. 35 is a plan and FIG. 36 is an elevation of an end portion of an inner bow component of a double facebow showing a guard structure somewhat similar to that of FIGS. 3 to 13, inclusive, but shaped somewhat differently. FIG. 37 is a plan corresponding to FIG. 35, and FIG. 38 is an end elevation corresponding to FIG. 36, of an end portion of an inner bow component of a double facebow showing the same guard structure but having parts in a different adjusted position.

FIG. 39 and FIG. 40 are top perspectives, and FIG. 41 is a plan of an end portion of an inner bow component of a double facebow showing still a different type of guard structure, FIGS. 40 and 41 showing the component of FIG. 39 in formed condition.

FIG. 42 is a top perspective of an end portion of an inner bow component of a double facebow showing a further modified guard-mounting structure.

FIG. 43 is a top perspective of an end portion of an inner bow of a double facebow showing bow structure and guard-mounting structure somewhat similar to that shown in FIG. 42 with a modified type of guard arrangement.

DETAILED DESCRIPTION

Figure 1:
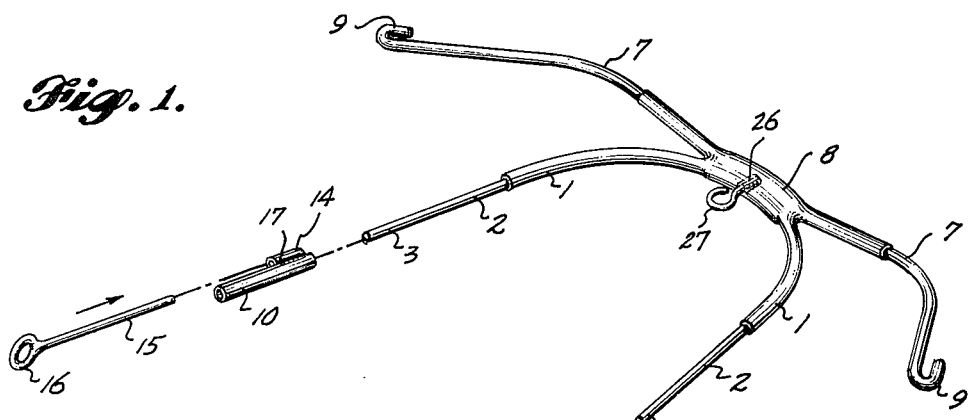
FIG. 1 is a top perspective of a double facebow and guards showing parts in exploded relationship.

The inner bow component of a conventional double facebow that is received within the mouth includes bifurcations 1 having reduced inner end shanks 2, the tips 3 of which are of small diameter wire such as 17 USS wire gauge, the diameter of which is 0.0540 inches (1.37 mm.), or 18 USS wire gauge, which is 0.475 inches (1.21 mm.) in diameter. Whether the end of wire of such size is square or chamfered or rounded or pointed, it is sharp in the sense that it is likely to pierce a body member such as a gun, a cheek, a lip or even an eye which it may jab.

When the inner bow is installed in the mouth of a patient, the inner bow shank wires 2 are connected to teeth. Such connection can be effected by inserting an anchor tip 3 into a socket tube 4 mounted on the outer side of a molar band 5 encircling a molar, as shown best in FIG. 9. A rearward thrust can then be applied to the inner body bifurcations 1 by applying a force to each of the oppositely projecting bifurcations 7 of the outer bow component of the double facebow. The central portions 8 of the outer bow and inner bow are joined integrally by soldering or welding. A rearward force can be exerted on this junction by pulling rearward on the hooks 9 on the outer ends of the outer bow bifurcations 7.

The rearward thrust of the inner bow bifurcations 1 produced by the pull on the outer bow hooks 9 can be transmitted from the inner bow shanks 2 to the molar band socket tubes 4 through stop sleeves 10 secured on the inner bow shanks 2 with their inner ends spaced from the ends of tips 3 sufficiently to leave such tips free to be inserted over substantially their full length into the sockets 4. Each sleeve 10 has a snug sliding fit on its bow shank 2. The inner diameter of such sleeve may be 0.001 or 0.002 inches (0.0254 to 0.0508 mm.) larger than the bow shank, and the wall thickness of the tube may be 0.006 inches (0.152 mm.). The length of such tube may be 0.5 to 0.6 inches (12.7 to 15.2 mm.) in length. Each sleeve 10 is secured to its inner bow shank 2 by spot welding, soldering or crimping the shank end tube so that the reaction of the socket 4 to the rearward pressure exerted on it by the sleeve 10 will not slide such sleeve forward on the shank 2 to prevent the anchor tip 3 from penetrating farther through the tubular socket 4.

Figure 3:
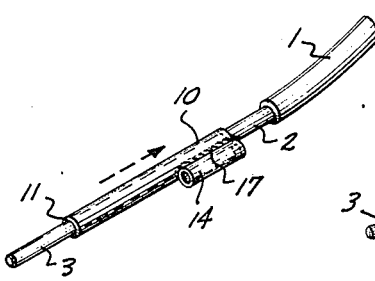
FIGS. 3, 4, 5, 6 and 7 are top perspectives of an end portion of the inner bow component of the double facebow illustrating different stages of applying a guard to such inner bow end portion.
Figure 4:
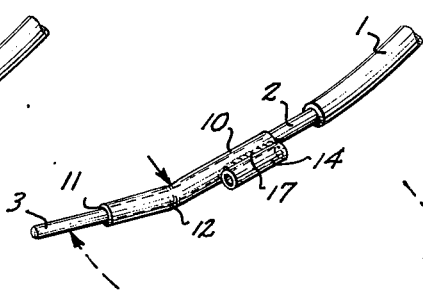
Figure 5:
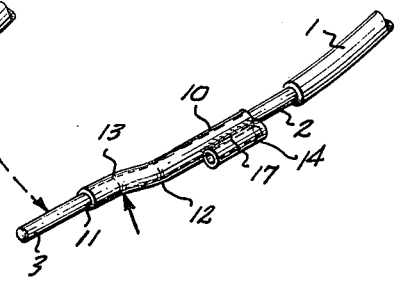
Figure 6:
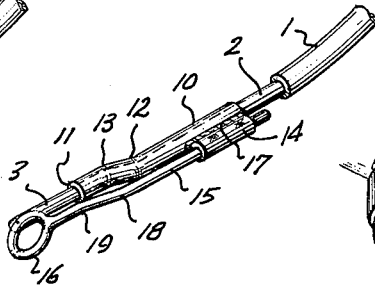

In FIGS. 3, 4 and 5, the sleeve 10 is illustrated as being secured to the inner bow shank 2 by offsetting such shank end tube which serves the further function of spacing the outer portion of the shank farther from the teeth. In FIG. 3 the tube and shank are shown as being straight so that the tube can be slid over the tip 3 onto the shank 2 until its inner end 11 is spaced from the end of tip 3 a distance approximately equal to the length of the molar band socket tube 4. The central portion of the tube 10 and inner bow shank 2 which it encircles can then be bent at 12 to deflect the inner portion of the sleeve inward, followed by bending the portion of the sleeve 10 and the shank within it in the opposite direction at 13 to deflect the portion of the tube and shank rearwardly of such bend in an outward direction.

Figure 9:
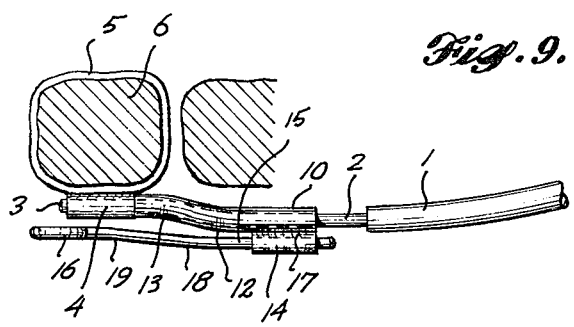
FIG. 9 is a plan.
Figure 11:
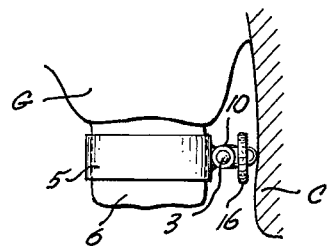
FIG. 10 is a side elevation and FIG. 11 is an end elevation of an endportion of an inner bow component installed in relation to teeth in the manner shown in FIG. 8.
Figure 10:
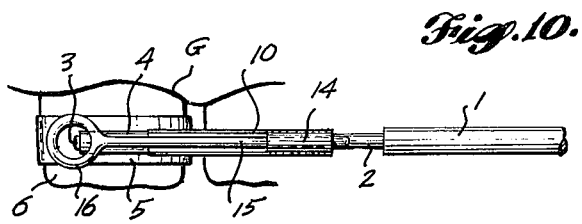

The offset formed by the opposite bends 12 and 13, shown best in FIG. 5, will locate the tip 3 of the inner bow for easy insertion into the molar band socket tube 4, as shown in FIG. 9. The tip may be tilted up or down by bending shank 2 or the root of tip 3. The rearward force then applied by the end 11 of sleeve 10 to the molar band socket tube will press the molar 6 rearward. If an arch wire is tied to such molar band and also to bands on the teeth forward of it, all of the teeth will be shifted rearwardly in the jawbone, or at least will be restrained from moving forward in the jawbone. The degree of force thus applied to the teeth will depend on the amount of pull exerted on the hooks 9 of the outer bow bifurcations 7.

If the rearward thrust exertedby the inner bow is reversed momentarily, such as by a pull being exerted on one or both of the outer bow bifurcations 7, one or both of the tips 3 may be pulled out of the corresponding molar socket tube or tubes 4. If the momentarily reversed force is then discontinued, such as by a direct pull on one or both bifurcations 7 being removed so that the pull on the hooks 9 is restored, the resumed thrust exerted on the inner bow when its tips 3 are not engaged in the socket tubes 4 could drive the entire facebow rearward so that the tips 3 would jab gum, inner cheek or other tissue in the inner portion of the mouth to penetrate it and cause injury.

A worse condition could occur if the momentary forward pull on the outer bow bifurcations 7 were sufficient to pull the inner bow entirely out of the mouth before such momentary pull is released, so that, when the pull reverts only to that applied to th outer bow hooks 9, the facebow would be propelled rearward jabbing the tips 3 into the outer cheeks, neck or perhaps even the eyes of the wearer. In such event very serious injury could occur, both because of the portions of the face that might be engaged and because the rearward force exerted on hooks 9 would be greater than if than if the inner bow had not been pulled out of the mouth, so that the jabbing action of the sharp tips 3 would be more forceful.

The purpose of the present invention is to provide a guard which will engage a body member toward which the inner bow tip is propelled instead of, or at least considerably before, the end of the sharp tip 3 can engage the body member. A mounting sleeve 14 for receiving the shank 15 of a cantilever guard wire is carried by each stop sleeve 10. Such sleeve can be approximately one-third of the length of sleeve 10 and receives the guard wire with a snug sliding fit. The end of the guard wire shank 15 remote from the sleeve 14 is an enlarged blunt end which can be formed as a symmetrical loop 16. Preferably the guard-mounting sleeve 14 is considerably shorter than the stop sleeve 10 and is secured to the outer end of such sleeve by welding 17 to form a double sleeve having the two sleeves in side-by-side relationship.

A representative installation of a guard wire is shown in FIGS. 6 to 11. After the tip 3 of the facebow shank 2 has been offset in the manner described above and shown in FIG. 5, the end of guard wire 15 remote from its enlarged end 16 is inserted into the sleeve 14 in the direction of the arrows shown in FIG. 1. When the guard wire end has been inserted through its mounting sleeve, the guard wire can be secured to the sleeve either at that time or later, such as by soldering or spot welding. It is preferred that the guard wire be connected to the sleeve by spot welding so that the guard wire and the sleeve can be disconnected without damaging either the guard wire or the sleeve by rotation of the guard wire sleeve relatively about their axes.

Figures 7, 8:
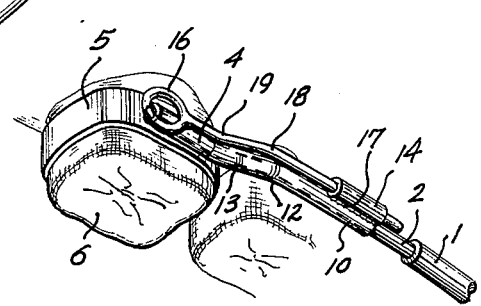
FIG. 8 is a bottom perspective of an end portion of an inner bow component of a double facebow showing such end portion installed relative to teeth.

Either before or after the end of the guard wire shank 15 has been inserted into its mounting sleeve 14, or before or after the guard wire has been anchored to such mounting sleeve, wichever is more convenient, the shank of the guard wire can be offset so that the enlarged blunt end portion of the guard wire will lie close alongside the molar socket tube 4 in which the anchor tip 3 is inserted. The guard wire can be offset generally corresponding to the offset of the stop tube 10 and shank 2 of the inner bow by a bend 18 deflecting the portion of the guard wire rearwardly of such bend in an inner direction and a bend 19 between the bend 18 and the rear end of the guard deflecting outward the portion of the guard rearward of such bend. FIGS. 8 and 9 illustrate how the bends 18 and 19 offset the enlarged blunt end portion 16 of the guard from the portion of the guard shank 15 received in the mounting sleeve 14 so that the blunt end of the guard will lie close alongside the tip 3.

Figure 12:
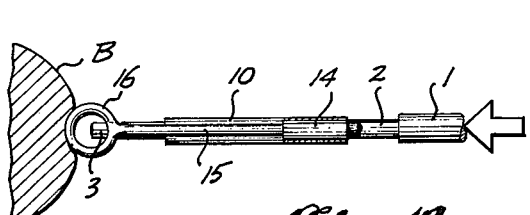
FIG. 12 is a side elevation and FIG. 13 is a plan of an end portion cf an inner bow component of a double facebow showing the guard engaged with a portion of a body such as an eye.
Figure 13:
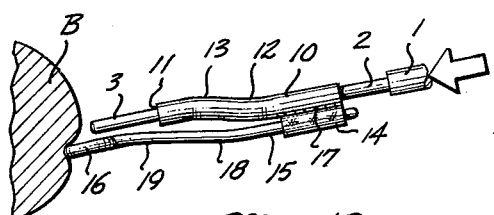

It is very important that the enlarged blunt end portion of the guard wire project rearwardly beyond the end of the tip 3 a substantial distance, as shown best in FIGS. 9, 12 and 13. If the inner bow is jabbed toward a body member B, such as an eye, in the direction indicated by the arrows in FIGS. 12 and 13, the blunt end portion of the guard shown as a loop will engage the body member so as to prevent the tip 3 from contacting the body member at all, or at least the blunt end portion of the guard will depress the body member so that, if the rear end of tip 3 ever reaches the body member, it will touch such member only lightly. While the enlarged blunt end portion of the guard may bruise the body member, its bluntness will deter the body member from being punctured, pierced, torn or scraped.

Figure 14:
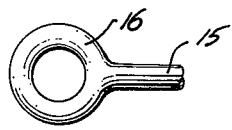
FIG. 14, FIG. 15 and FIG. 16 are side elevations of end portions of a guard wire illustrating different types of loops for forming enlarged blunt end portions.
Figure 15:
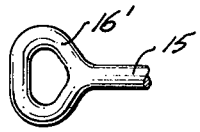
Figure 16:
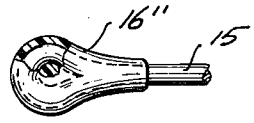

While FIGS. 6 to 13, show the enlarged blunt end portion of the guard member as being a circular loop, the particularly type of loop can vary, as illustrated by the loops shown in FIGS. 14, 15 and 16, for example. The loop 16 of FIG. 14 is of the circular type, but either the stock of which it is made is shown as being of somewhat larger cross section than the stock used for making the loop shown in FIGS. 1, 6 to 8, and 10 or the diameter of the loop is somewhat smaller. In FIG. 15, the loop 16' is flattened transversely of the guard shank. The loop 16" of FIG. 16 is encased in a plastic coating which preferably is of resilient character.

The application of a guard wire of the type described above does not prevent the inner bow of the double facebow from being refitted to the patient's mouth from time to time as may be required as the orthodontic treatment progresses, or from being fitted to a different patient. The inner bow shank 2 and stop sleeve 10 are sufficiently malleable so that the offsetting bends 12 and 13 in the stop sleeve and the facebow shank 2 within it can be straightened to enable the stop sleeve to be slid lengthwise of the inner bow shank again. In such a refitting operation, it is desirable first to straighten the guard wire shank 15 and then to twist it relative to the mounting sleeve 14 so as to break the spot welds or other bond for enabling the guard wire to be withdrawn from the mounting sleeve.

Figure 17:
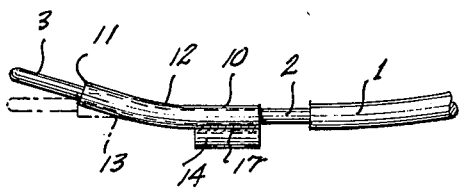
FIGS. 17 and 18 are plans of end portions of an inner bow component of a double facebow similar to those shown in FIGS. 3 to 7, inclusive, illustrating procedure for adjustment of parts of the composite structure.
Figure 18:
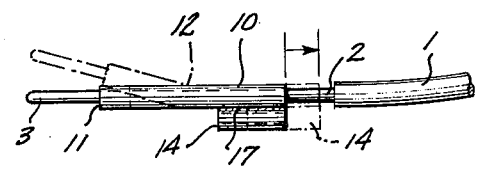

The farther rearward bend 13 of the stop sleeve 10 and the portion of the inner bow shank 2 within it can now be straightened from the broken line position to the solid line position shown in FIG. 17, then the farther forward bend 12 can be straightened from the condition shown in broken lines in FIG. 18 to the straight condition shown in solid lines. Next the double sleeve 10, 14 can be slid along the inner bow shank 2 in the direction indicated by the arrow in FIG. 18 to shorten the inner bow. The free end portion of the tip 3 can then be cut off so that the same length of tip will project beyond the end 11 of the stop sleeve as before the double sleeve was shifted along the inner bow shank. To anchor the stop sleeve 10 on the portion of the inner bow shank 2 within it again, such parts can be rebent into the offset condition of FIG. 5 in the manner described with reference to FIGS. 3 and 4.

Alternatively, after the sleeve 10 and bow shank 2 have been straightened, the sleeve may be slid rearward on the shank 2 for a short distance to increase the effective length of the bow bifurcation. In that case the guard wire shank 15 can be slid forward somewhat to reposition the loop 16 relative to the tip 3 in the same position it was before.

Figure 19:
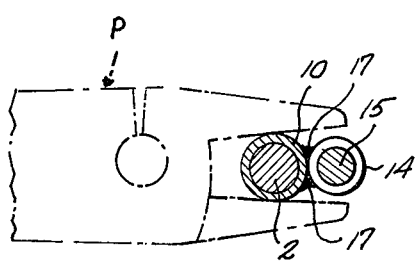
FIG. 19 is a transverse section through an end portion of an inner bow component of a double facebow illustrating a manipulative operation of such structure.

A preferred type of inner bow shank, guard and double sleeve are shown in FIG. 19. The wire forming the inner bow shank 2 is larger than the guard wire 15, and the difference in size may be one gauge number. Thus if the inner bow shank wire 2 is of 17 gauge (0.0540 of an inch or 0.37 mm in diameter), the guard wire 15 would be 18 gauge (0.0475 of an inch or 1.21 mm. in diameter). If the wire of the inner bow shank were 18 gauge, the guard wire would be 19 gauge (0.0410 of an inch or 1.04 mm in diameter). The wall thickness of the sleeve 14 is approximately equal to the wall thickness of the sleeve 10, or perhaps slightly less. Consequently, the stop sleeve 10 is of larger diameter than the guard-mounting sleeve 14. If the sleeve 10 is grasped by pliers P, as shown in broken lines, to manipulate it, such as to slide it along bow shank 2, there is no danger of the pliers crushing or deforming sleeve 14 so that a guard wire cannot be inserted into it easily. Such proportioning of the wire sizes of inner bow shank 2 and guard wire shank 15 also would enable the inner bow shank or its tip 3 to be gripped and held by a pair of pliers without gripping the guard wire shank.

In FIGS. 20 to 27, the double sleeve 10, 14' can be the same as that shown in FIGS. 3 to 13, inclusive, but in this instance, the double sleeve is secured on the inner bow shank 2 so that the guard-mounting sleeve 14' is mounted on the upper side of the stop sleeve 10 when the inner bow is to be attached to teeth of the upper jaw, instead of the guard-mounting sleeve being on the outer side of the stop sleeve. If the inner bow were to be attached to teeth of the lower jaw, the guard-mounting sleeve could be secured to the lower side of the stop sleeve. Disposition of the guard-mounting sleeve over or under the stop sleeve, instead of being located on the outer side of the stop sleeve, reduces the possibility of the guard-mounting sleeve contacting the wearer's cheek.

Moreover, such over or under location of the guard-mounting sleeve improves access to the stop sleeve for shaping purposes. With the guard wire 15 located principally overlying the stop sleeve 10, as shown in FIG.

23, the opposite sides of the stop sleeve are much more readily accessible to pliers P, as shown in FIG. 21, than the sleeve 10 in FIG. 7. Such pliers can be of the four-jaw type including two spaced jaws $P_1$ and $P_2$ at one side of the stop sleeve and spaced jaws $P_3$ and $P_4$ at the opposite side of the stop sleeve. Such jaws are arranged so that the jaw $P_3$ is centered between the jaws $P_1$ and $P_2$ and the jaw $P_2$ is centered between the jaws $P_3$ and $P_4$.

The jaws $P_1$ and $P_2$ of the pliers P and the jaws $P_3$ and $P_4$ of such pliers are spaced apart a distance relative to the diameter of the stop sleeve 10 such that simultaneous pressure of all four jaws will produce two bends 12 and 13 effecting an offset in the stop sleeve. By the use of four-jaw pliers, bending of such offset can be accomplished by a single application of the pliers. The degree of offset can be altered to some extent by the amount of pressure applied to the pliers. Alternatively, the bends can be made separately and sequentially by using three-jaw pliers such as shown in FIGS. 26 and 27.

Even with the guard-mounting sleeve 14' located over the stop sleeve 10, as shown in FIGS. 20 to 27, inclusive, it is desirable for the enlarged blunt end portion of the cantilever guard wire remote from the mounting sleeve to be disposed alongside the tip 3 of the inner bow shank 2, as shown best in FIGS. 21 and 23. Such location of a guard wire end loop can be accomplished more readily by the loop 20 being underslung instead of arranged symmetrically with respect to the guard wire, as shown best in FIG. 23. In addition to making the loop underslung, it may be desirable for the opposite ends of the guard wire to be displaced circumferentially of the tooth-connectible inner bow shank 2 to a greater or lesser extent.

The assembly of the structure shown in FIGS. 21 to 23 follows generally the sequence described in connection with FIGS. 3 to 11. The double sleeve 10, 14' is assembled with the inner bow shank 2 by sliding the stop sleeve 10 over the tip 3 in the direction indicated by the arrow, and the guard wire shank 15 is inserted into the guard wire-mounting sleeve 14' by movement of the guard in the direction indicated by the arrow in FIG. 20. The stop sleeve 10 may be placed on the inner bow shank 2 before or after the guard has been assembled with the double sleeve. Also, in order to dispose the underslung loop 20 alongside the tip 3 of the inner bow shank, as shown in FIG. 21, a bend 21 can be made in the guard wire at a location adjacent to the loop 20, as shown in FIGS. 20, 21 and 22. Such bend can be made before or after the guard is assembled with the double sleeve.

While the stop sleeve 10 can be anchored to the inner bow shank 2 by bonding or spot welding, alternatively the stop sleeve can be anchored against movement relative to the inner bow shank 2 simply by crimping the stop sleeve 10 and shank 2, such as by the bends 12 and 13 forming the offset in these parts. Also, while the guard wire shank 15 can be anchored to the sleeve 14' simply by spot welding, it may be desirable to provide additional means for preventing the guard wire shank and the sleeve 14' from being separated while permitting the guard wire to slide relative to the sleeve, for the purposes described below. Such connection of the guard wire and sleeve can be effected by flattening or otherwise upsetting the end portion 22 of the guard wire at the end of the sleeve remote from the loop 20 after the guard wire is inserted through the sleeve sufficiently so that the guard wire cannot be pulled out of the sleeve.

Before the guard wire shank 15 and the guard-mounting sleeve 14' are secured together by spot welding, such as indicated in FIGS. 22 and 23, or after such spot-welds have been broken by relative rotation of the guard wire shank and the mounting sleeve about their axis, the guard wire shank and the mounting sleeve can be shifted relatively longitudinally between the position shown in FIGS. 21, 22 and 23, and the position shown in FIGS. 24 and 25. With the guard in the position of FIGS. 24 and 25, the bends 12 and 13 of the stop sleeve 10 are even more readily accessible for refitting of the inner bow. In this construction, the guard cannot be removed nondestructively. However, because of its slidability, it need not be removed for refitting the inner bow. The guard wire can be replaced, if necessary, by cutting off the enlargement 22.

FIGS. 26 and 27 illustrate the use of pliers P having three jaws including a jaw $P_5$ at one side of the pliers centered between a pair of jaws $P_6$ at the opposite side of the pliers. By crimping the stop sleeve 10 between the opposed jaws of the pliers, a bend 12 or a bend 13 can be formed in the stop sleeve, and shank 2 of the inner bow within it, at any desired location as illustrated by FIGS. 26 and 27. If the jaws of the pliers are short, as shown in FIG. 26, such crimping can be effected easily even though the guard is in the position of FIGS. 21 to 23.

FIG. 28 shows the appliance of FIGS. 20 to 27, inclusive, connected to teeth for orthodontic treatment. The tip 3 of the inner bow shank 2 is inserted into the socket tube 4 of the band 5 encircling the molar 6 in the manner shown and previously described in connection with FIGS. 8 and 9. The bend 21 locates the enlarged blunt end portion 20 of the guard close alongside the molar band socket tube. While the loop 20 projects beyond the tip 3 of the shank 2, it does not project rearwardly beyond the molar. Consequently, the guard is quite unobtrusive and will not cause appreciable annoyance or discomfort.

The inner bow end and attached guard shown in FIG. 29 is very similar to the structure shown in FIGS. 22, 23 and 28. The only difference is that the end 22' of the guard wire 15, instead of being flattened to enlarge it like the guard wire end 22 of FIGS. 22, 23 and 28, is simply bent inward beyond the end of the guard-mounting sleeve 14 so as to prevent the guard wire shank 15 from being withdrawn from the sleeve 14.

In the structure of FIGS. 30, 31 and 32, the guard wire shank 15' is attached directly to the stop sleeve 10 instead of being received in a guard-mounting sleeve. The shank end portion 23 is located in a position overlying the forward end of the stop tube and is anchored by welding 17' directly to the stop tube. While mounting the guard wire on the stop tube in this fashion prevents the guard wire from being separated from the stop tube or adjusted lengthwise of the stop tube, such adjustment is not essential and the guard mounting of FIGS. 30, 31 and 32 is more compact and less obtrusive than the mounting which utilizes a guard-mounting sleeve 14'. With this type of construction, if the sleeve 10 and inner bow shank 2 are straightened and the sleeve is moved forward slightly, the underslung loop 20 can be uncoiled to a small extent to move the loop effectively rearward so as to maintain the same relationship to the rearward end of tip 3. Conversely, if the sleeve 10 is moved slightly rearward on inner bow shank 2, loop 20 can be rolled up to a small extent to restore its relationship to the rearward end of tip 3.

In all of the structures of FIGS. 21 to 28, of FIG. 29 and of FIGS. 30 to 32, it is desirable for the enlarged end loop 20 to be located as close alongside the tip 3 as possible without interferring appreciably with the operation of inserting the inner bow tip 3 into the molar band socket tube 4. In fitting the inner bow end, the bend 12 and the bend 13 may not be exactly the same. Consequently, the tip 3 may not be parallel to the guard-mounting sleeve 14' or to the anchored end portion 23 of the guard wire shank of FIGS. 30, 31 and 32. After the inner end of the inner bow has been fitted for connection of the tip 3 to the socket tube 4 of the molar band 5, the position of the guard loop 20 can be adjusted by bending the guard wire shank 15'. If it is desired to move the loop closer to the tip 3, a bend 21, such as shown in FIG. 21, can be made in the guard wire shank. On the other hand, if it is desired to move the loop 20 farther from the tip 3, an offset bend 24 shown in FIGS. 31 and 32 can be made in the guard wire shank 15'. Alternatively, any combination of such bends can be made.

Instead of anchoring the guard wire end portion 23 to the top of the stop tube 10, as shown in FIGS. 30 and 31, the end portion 23' of the guard wire shank 15 can be attached to the side of the stop tube 10 by welding 17', as shown in FIGS. 33 and 34. In a guard structure of this type, the enlarged blunt end portion would be a symmetrical loop 16, as shown and described in connection with FIGS. 1 and 6 to 16. The stop tube can be installed on the shank 2 of an inner bow bifurcation 1, as shown in FIG. 34 and described in connection with FIGS. 3, 4 and 5. The spacing between the guard eye 16 and the inner bow tip 3 can be adjusted as desired by making an offset bend 24' in the guard shank 15 or otherwise bending the guard shank.

In FIGS. 35 to 38, the same guard wire structure as in FIGS. 6 to 11, is shown. In this instance, however, the cantilever guard wire shank 15 is curved gradually throughout its length between the eye 16 and the portion of the shank received in the guard-mounting sleeve 14. While the inner bow end is being fitted in the mouth, the guard wire can be turned to the position of FIGS. 35 and 36 in which the guard wire sweeps outward from the guard-mounting sleeve 14 to engage the cheek C and hold it away from the inner bow end being fitted.

After the fitting has been completed, the guard shank 15' can be rotated 180° relative to mounting sleeve 14 about the axis of such sleeve so that the eye 16 will be moved inward to the position shown in FIGS. 37 and 38. Thereafter, the doctor or patient can remove and insert the inner bow because, in that rotated position of the guard there will still be reasonable clearance between the guard eye and the inner bow tip 3 to enable such tip to be inserted into the socket tube 4 of the molar band 5. With the guard in that position, either the guard will clear the cheek under normal conditions, as illustrated in FIG. 38, or the cheek will lie smoothly against the guard, as illustrated in FIG. 37. In either instance, abrasion or irritation of the wearer's cheek will be minimized.

The inner bow end portion shown in FIGS. 40 to 43, inclusive, has a shank 2 of a sufficient length, as shown in FIG. 39, to enable an omega bend 25 to be made in such shank. In the type of inner bow end portion shown in FIGS. 40 and 41, such omega bend is engageable with the molar socket tube 4 into which the tip 3 is inserted to serve as a stop in place of the stop sleeve 10. With this type of construction, it is preferred that the guard-mounting sleeve 14" be carried by the rearward end of the sleeve 10, as shown in FIGS. 39, 40 and 41, instead of by the forward end of such sleeve.

In the type of inner bow structure shown in FIGS. 42 and 43, the omega loop 25 is spaced farther from the end of the inner bow so that a stop sleeve is mounted on the inner bow shank between the omega loop and the tip 3. In FIG. 42, the stop sleeve 10' is much shorter than the stop sleeve 10 described above and carries an even shorter guard-mounting sleeve 14. This sleeve is secured to the stop sleeve 10' by welding 17.

The guard mounted in the sleeve 14 will have a shank 15" much shorter than the shanks 15 or 15' of the guards described above. The guard shank has a short offset bend 24" to space the guard loop 16 adequately from the tip 3. Because of the compact character of the structure shown in FIG. 42, the stop sleeve 10' is secured to the inner bow shank 2 by spot welding or bonding rather than crimping. The end portion of the guard wire shank 15" is also spot welded to the mounting sleeve 14.

The guard structure shown in FIG. 43 differs from that of FIG. 42 in that the end portion 23' of the guard wire shank 15" is secured directly to the side of the inner bow shank 2 by welding 17'. A very short stop tube 10" is spot welded to the inner bow shank 2 between the end portion 23' of the guard shank 15" and the tip 3. The guard shank has an abrupt offset bend 24" adjacent to the stop tube 10" to space the guard loop 16 outward from the inner bow tip 3 so as to afford sufficient clearance for such tip to be inserted into a molar band socket tube 4 in the manner described above.

Figure 2:
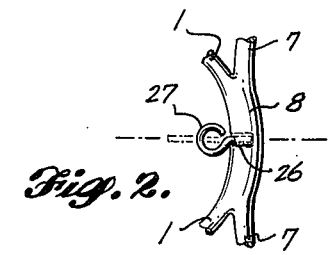
FIG. 2 is a fragmentary plan of a portion of a double facebow having a spur according to the present invention.

Up to this point, the specific guards described have been located alongside sharp projections formed by the tips 3 of the inner bow bifurcations 1 of a double facebow. In some instances the midline spur 26 shown in FIGS. 1 and 2 is provided projecting inward from the junction of the inner bow and outer bow to engage beneath the central portion of an orthodontic arch wire for the purpose of exerting an intrusive force on the banded upper incisors. Such a spur usually is made of 17 gauge or 18 gauge wire which is 0.0540 inches (1.37 mm.) or 0.0475 inches (1.21 mm.), and therefore is sharp even though it has a square or rounded end.

As has been described above, if a pulling force is exerted on one or both bifurcations 7 of the outer bow to a degree sufficient to overcome the rearward pulling force exerted on hooks 9 and to withdraw the tips 3 from the molar socket tubes 4 and the forward pulling force is then released, the rearward pulling force exerted on the hooks 9 can snap the double facebow inward so that the tips 3 could penetrate intraoral tissue. Alternatively, or simultaneously, a sharp midline spur 26 could jab and pierce the front gums or, if withdrawn outside of the mouth, could jab and pierce the lips or even the nose.

In order to eliminate, or at least minimize, injury to the wearer of a facebow from such manipulation, the midline spur 26 of the present invention has an enlarged blunt end portion shown as being in the form of a loop 27 which can be of approximately the same size as the loops 16 on the side guards. In order to enable the midline spur to exert an upward force reliably on the central portion of an arch wire, the plane of the loop 27 should be disposed substantially parallel to the plane of the inner bow. The effective length of the spur can be adjusted slightly by enlarging the loop to reduce the spur length or decreasing the loop to lengthen the spur. A still more reliable engagement of the midline spur with an arch wire can be obtained if the rearward side of the midline spur loop were flattened, as shown in loop 16' of FIG. 15.

I claim:

1. A guard for an intraoral orthodontic appliance including an arch wire having a rearwardly projecting end portion for insertion in a tubular socket of a tooth attachment, comprising guard means including a guard wire shank having a blunt end portion substantially larger than the rearwardly projecting arch wire end portion, and mounting means mounting said guard means on the arch wire with said guard wire shank extending alongside the rearwardly projecting arch wire end portion in generally parallel relationship to such arch wire end portion and spaced laterally therefrom a distance sufficient to receive a side of such tubular socket between said guard wire shank and such arch wire end portion, said guard wire shank blunt end portion extending rearwardly at least as far as the arch wire rearward end portion for shielding the rearwardly projecting arch wire end portion against jabbing by rearward movement of the arch wire.

2. The guard defined in claim 1, the guard wire shank blunt end portion being a wire loop.

3. The guard defined in claim 1, the mounting means bonding the guard means directly to the arch wire.

4. The guard defined in claim 1, the mounting means bonding the guard means directly to the outer side of the arch wire.

5. The guard defined in claim 1, the mounting means including a sleeve mounted on the arch wire and receiving carrying the guard means.

6. The guard defined in claim 1, the mounting means including a sleeve receiving the arch wire and carrying the guard means.

7. The guard defined in claim 6, the mounting means bonding the guard means directly to the sleeve.

8. The guard defined in claim 6, the mounting means bonding the guard means directly to the outer side of the sleeve.

9. The guard defined in claim 6, the mounting means bonding the guard means directly to the upper side of the sleeve.

10. The guard defined in claim 1, a first sleeve receiving the arch wire, and a second sleeve carried by said first sleeve and carrying the guard means.

11. The guard defined in claim 10, the first sleeve being of greater width than the second sleeve.

12. The guard defined in claim 10, the second sleeve being shorter than the first sleeve.

13. The guard defined in claim 10, the second sleeve being secured to the outer side of the first sleeve.

14. The guard defined in claim 10, the second sleeve being secured to the upper side of the first sleeve.

15. The guard defined in claim 1, the mounting means mounting the guard means on the outer side of the arch wire and the guard wire shank blunt end portion being a symmetrical wire loop.

16. The guard defined in claim 1, the mounting means mounting the guard means on the upper side of the arch wire and the guard wire shank blunt end portion being an underslung wire loop.

17. The guard defined in claim 5, the arch wire having in it an omega loop and the sleeve mounted on the arch wire being located at the side of said omega loop remote from the rearward end of the arch wire.

18. The guard defined in claim 5, the arch wire having in it an omega loop and the sleeve being mounted on the arch wire at a location between said omega loop and the rearward end of the arch wire.

19. The guard defined in claim 3, the arch wire having in it an omega loop, and the mounting means bonding the guard means directly to that portion of the arch wire between said omega loop and the rearward end of the arch wire.

20. The guard defined in claim 1, the guard wire shank blunt end portion including a wire having a plastic coating.

21. In an intraoral orthodontic appliance the combination of an arch wire having a rearwardly projecting end portion for insertion in a tubular socket of a tooth attachment, guard means including a guard wire shank having a blunt end portion substantially larger than the rearwardly projecting arch wire end portion, and means mounting said guard means on the arch wire with said guard wire shank extending alongside said rearwardly projecting arch wire end portion and projecting rearwardly therebeyond.

22. A guard for an intraoral orthodontic appliance having a projection with a sharp end, comprising guard means having a blunt end portion substantially larger than the projection sharp end, and mounting means mounting said guard means on the projection with said blunt end portion shielding the projection sharp end without covering such sharp end.

23. A guard for an orthodontic double facebow including an inner bow and an outer bow having their central portions joined, the inner bow having a midline spur on its inner side, comprising guard means forming an enlarged blunt end on the midline spur.

* * * * *

UNITED STATES PATENT OFFICE
CERTIFICATE OF CORRECTION

Patent No. 4,038,754  Dated August 2, 1977

Inventor(s) Maclay M. Armstrong

It is certified that error appears in the above-identified patent and that said Letters Patent are hereby corrected as shown below:

Column 11, lines 35 and 36, cancel "receiving".

Signed and Sealed this

Fifteenth Day of November 1977

[SEAL]

Attest:

RUTH C. MASON
Attesting Officer

LUTRELLE F. PARKER
Acting Commissioner of Patents and Trademarks